US012564416B2

(12) United States Patent
Klein

(10) Patent No.: US 12,564,416 B2
(45) Date of Patent: Mar. 3, 2026

(54) SURGICAL INSTRUMENTS WITH ELECTRICALLY ISOLATED ACTUATION MEMBERS, RELATED DEVICES, AND RELATED METHODS

(71) Applicant: INTUITIVE SURGICAL OPERATIONS, INC., Sunnyvale, CA (US)

(72) Inventor: Jordan M. Klein, Palo Alto, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1179 days.

(21) Appl. No.: 16/317,276

(22) PCT Filed: Jun. 29, 2017

(86) PCT No.: PCT/US2017/040005
§ 371 (c)(1),
(2) Date: Jan. 11, 2019

(87) PCT Pub. No.: WO2018/013354
PCT Pub. Date: Jan. 18, 2018

(65) Prior Publication Data
US 2019/0290310 A1      Sep. 26, 2019

Related U.S. Application Data

(60) Provisional application No. 62/362,447, filed on Jul. 14, 2016.

(51) Int. Cl.
*A61B 18/14* (2006.01)
*A61B 17/29* (2006.01)
(Continued)

(52) U.S. Cl.
CPC .......... *A61B 17/2909* (2013.01); *A61B 18/14* (2013.01); *A61B 18/1445* (2013.01);
(Continued)

(58) Field of Classification Search
CPC ...... A61B 2017/00336; A61B 18/1445; A61B 34/30; A61B 2017/2901–2922
See application file for complete search history.

(56) References Cited

U.S. PATENT DOCUMENTS 5,810,876 A * 9/1998 Kelleher ................ A61B 10/06
606/205
6,673,087 B1 * 1/2004 Chang ............ A61B 17/320016
606/174
(Continued)

FOREIGN PATENT DOCUMENTS

WO      WO-03001987 A2      1/2003
WO      WO-2015023865 A1      2/2015
(Continued)

OTHER PUBLICATIONS

International Search Report and Written Opinion for Application No. PCT/US2017/040005, mailed on Oct. 6, 2017, 16 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Linda C Dvorak
*Assistant Examiner* — Christine A Dedoulis
(74) *Attorney, Agent, or Firm* — Jones Robb, PLLC

(57) ABSTRACT
An actuation member for transmitting force from a drive mechanism to an end effector of a surgical instrument includes an electrically conductive distal flexible portion configured to be operably coupled with an end effector of a surgical instrument and an electrically conductive proximal rod portion connected to the flexible distal portion. The proximal rod portion is configured to be operably coupled to a drive mechanism. An electrically insulating material sur-
(Continued)

DISTAL ◄-------► PROXIMAL rounds at least a portion of a length of the distal flexible portion and at least a portion of a length of the proximal rod portion. The electrically insulating material extends at least over a location where the distal flexible portion and the proximal rod portion connect. Surgical instruments include such actuation members. Methods relate to configuring actuation members.

17 Claims, 9 Drawing Sheets

(51) Int. Cl.
  *A61B 34/00*    (2016.01)
  *A61B 34/30*    (2016.01)
  *A61B 17/00*    (2006.01)
  *A61B 18/00*    (2006.01)
(52) U.S. Cl.
  CPC ....  *A61B 34/70* (2016.02); *A61B 2017/00323*
      (2013.01); *A61B 2017/00336* (2013.01); *A61B*
          *2017/00367* (2013.01); *A61B 2017/00477*
      (2013.01); *A61B 2017/00929* (2013.01); *A61B*
          *2017/2902* (2013.01); *A61B 2017/2918*
      (2013.01); *A61B 2017/2944* (2013.01); *A61B*
          *2018/00077* (2013.01); *A61B 2018/00083*
          (2013.01); *A61B 34/30* (2016.02)

(56)            References Cited

U.S. PATENT DOCUMENTS

| | | | |
|---|---|---|---|
| 7,066,926 B2 * | 6/2006 | Wallace | A61B 34/70 |
| | | | 606/1 |
| 7,367,973 B2 * | 5/2008 | Manzo | A61B 34/37 |
| | | | 606/49 |
| 8,852,208 B2 | 10/2014 | Gomez et al. | |
| 2005/0182298 A1 | 8/2005 | Ikeda et al. | |
| 2006/0048787 A1 | 3/2006 | Manzo et al. | |
| 2006/0079884 A1 * | 4/2006 | Manzo | A61B 34/30 |
| | | | 606/41 |
| 2008/0021278 A1 * | 1/2008 | Leonard | A61B 17/1608 |
| | | | 600/129 |
| 2013/0325031 A1 | 12/2013 | Schena et al. | |
| 2013/0325033 A1 | 12/2013 | Schena et al. | |
| 2014/0128886 A1 | 5/2014 | Holop et al. | |
| 2014/0135793 A1 * | 5/2014 | Cooper | A61B 34/35 |
| | | | 606/130 |
| 2014/0338477 A1 * | 11/2014 | Donlon | F16H 19/001 |
| | | | 74/89.14 |

FOREIGN PATENT DOCUMENTS

| WO | WO-2018012398 A1 | 1/2018 |
|---|---|---|
| WO | WO-2018013217 A1 | 1/2018 |

* cited by examiner

234

232

230

PROXIMAL

DISTAL

241

242

DISTAL ⟵⟶ PROXIMAL

DISTAL ⟵⟶ PROXIMAL

DISTAL ⟷ PROXIMAL

DISTAL ← → PROXIMAL

PROXIMAL ← → DISTAL

SURGICAL INSTRUMENTS WITH ELECTRICALLY ISOLATED ACTUATION MEMBERS, RELATED DEVICES, AND RELATED METHODS

CROSS-REFERENCE TO RELATED APPLICATIONS

This application is a U.S. national stage application under 35 U.S.C. § 371(c) of International Application No. PCT/US2017/040005, filed on Jun. 29, 2017, which claims priority to U.S. Provisional Application 62/362,447, filed Jul. 14, 2016, each of which is incorporated by reference herein in its entirety.

TECHNICAL FIELD

Aspects of the present disclosure relate to surgical instruments including electrically isolated actuation members.

INTRODUCTION

Various surgical instruments or tools can be configured to apply electrical energy to an operating site to carry out a surgical procedure. For example, a surgical instrument may be configured to seal, bond, ablate, fulgurate, etc. tissue through the application of an electrical current. In some cases, the body of a patient is held at a ground (e.g., zero) electrical potential, while a portion of the surgical instrument is brought to a different electrical potential (e.g., by an operator command to the surgical system) to deliver electrical energy to the surgical site. Such surgical instruments and tools may include, without limitation, teleoperated and/or minimally invasive surgical systems. One example of a teleoperated, computer-assisted surgical system (e.g., a robotic system that provides telepresence), is the da Vinci® Surgical System manufactured by Intuitive Surgical, Inc. of Sunnyvale, Calif.

Often, other energized or non-energized surgical tools are in use at the surgical site. Such surgical tools frequently include components comprising conductive materials, such as, for example, metals or metal alloys. In particular, many surgical tools include actuation members, such as cables, rods, etc., or combinations thereof configured to transmit tensile and/or compressive forces between a force transmission device operably coupled at a proximal end of a surgical instrument shaft and an end effector operable coupled at a distal end of the surgical instrument shaft. Such components may comprise metals or metal alloys. If an energized tool is close to, or touching, a conductive, non-energy delivering tool using such components, the electrical energy from the energy delivering tool may flow into the non-energy delivering tool, e.g., through conductive components in contact with the actuation member. The electrical energy may be thereby misdirected from the intended application site.

Providing electrical insulation for such tools may be difficult for various reasons. For example, surgical instruments such as clamps, forceps, grippers, shears, etc. are often configured to deliver relatively high magnitudes of force to carry out desired surgical operations. To withstand such forces and provide durability, the actuation members of such surgical tools may be constructed from metals or metal alloys such as stainless steel, titanium alloys, aluminum alloys, etc., based on material properties such as yield strength, toughness, hardness, etc. Such materials, however, are typically relatively highly electrically conductive. Materials with electrical insulating properties, such as, e.g., polymers (e.g., plastics) and ceramics, may not have the desired combination of material properties such as yield strength toughness, hardness, wear resistance, etc. to use and wear resistance necessary for the actuation element.

A need exists to provide an electrically isolated surgical instrument without compromising the durability or reliability of the instrument. A need exists to continue to use relatively strong metal or metal alloy materials for actuation members while preventing undesirable electrically conductive pathways in a surgical instrument.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, an actuation member for transmitting force from a drive mechanism to an end effector of a surgical instrument includes an electrically conductive distal flexible portion configured to be operably coupled with an end effector of a surgical instrument and an electrically conductive proximal rod portion connected to the flexible distal portion, the proximal rod portion being configured to be operably coupled to a drive mechanism. The actuation member further includes an electrically insulating material surrounding at least a portion of a length of the distal flexible portion and at least a portion of a length of the proximal rod portion. The electrically insulating material extends at least over a location where the distal flexible portion and the proximal rod portion connect.

In accordance with at least another exemplary embodiment, a surgical instrument includes a shaft having a proximal end and a distal end, an end effector coupled to and extending distally from the distal end of the shaft, a force transmission mechanism coupled to the proximal end of the shaft, and an actuation member extending through a central bore of the shaft from the proximal end to the distal end of the shaft. The actuation member includes an electrically conductive distal flexible portion operably coupled to the end effector, an electrically conductive proximal rod portion connected to the distal flexible portion and operably coupled to the force transmission mechanism, and an electrically insulating material surrounding at least a location where the distal flexible portion and the proximal rod portion are connected to each other.

In accordance with yet another exemplary embodiment, a method of configuring an actuation member for transmitting force from a drive mechanism to an end effector of a surgical instrument includes connecting a proximal end of a distal flexible portion to a distal end of a proximal rod portion, each of the distal flexible portion and the proximal rod portion comprising an electrically conductive material, disposing a first electrically insulating material around at least a portion of a length of the distal flexible portion, and disposing a second electrically insulating material around at least a portion of a length the proximal rod portion and so as to at least partially overlap with the first electrically insulating material.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

The present disclosure contemplates various exemplary embodiments of surgical instruments and related devices configured for electrical isolation between portions of a component of the surgical instrument that comprises an electrically conductive material. For example, according to exemplary embodiments of the disclosure, a surgical instrument may include an actuation member comprising an electrically conductive material, (e.g., a metal and/or metal alloy) with an electrically insulating material covering at least a portion of the metal and/or metal alloy. In some exemplary embodiments, the actuation member includes at least a flexible cable portion and a rod portion coupled with the flexible cable portion, at least a portion of the cable and the rod being covered with the electrically insulating material. A distal end of the actuation member interfaces with a portion of an end effector to actuate the end effector. For example, the actuation member may include a component at a distal end of the cable portion configured to interact with the end effector for actuation thereof.

Exemplary embodiments of the disclosure provide actuation members configured for electrical isolation between a distal end portion and a proximal end portion. Such actuation members may prevent (e.g., eliminate) unintended conduction of electrical energy between the actuation member and other conductive components of the surgical instrument or regions external to the instrument.

Exemplary embodiments described herein may be used, for example, with teleoperated, computer-assisted surgical systems (sometimes referred to as robotic surgical systems) such as those described in, for example, U.S. Patent App. Pub. No. US 2013/0325033 A1, entitled "Multi-Port Surgical Robotic System Architecture" and published on Dec. 5, 2013, U.S. Patent App. Pub. No. US 2013/0325031 A1, entitled "Redundant Axis and Degree of Freedom for Hardware-Constrained Remote Center Robotic Manipulator" and published on Dec. 5, 2013, and U.S. Pat. No. 8,852,208, entitled "Surgical System Instrument Mounting" and published on Oct. 7, 2014, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. Although various exemplary embodiments described herein are discussed with regard to surgical instruments used with a patient side cart of a teleoperated surgical system, the present disclosure is not limited to use with surgical instruments for a teleoperated surgical system. For example, various exemplary embodiments of actuation members described herein can optionally be used in conjunction with hand-held, manual surgical instruments.

Figure 1A:
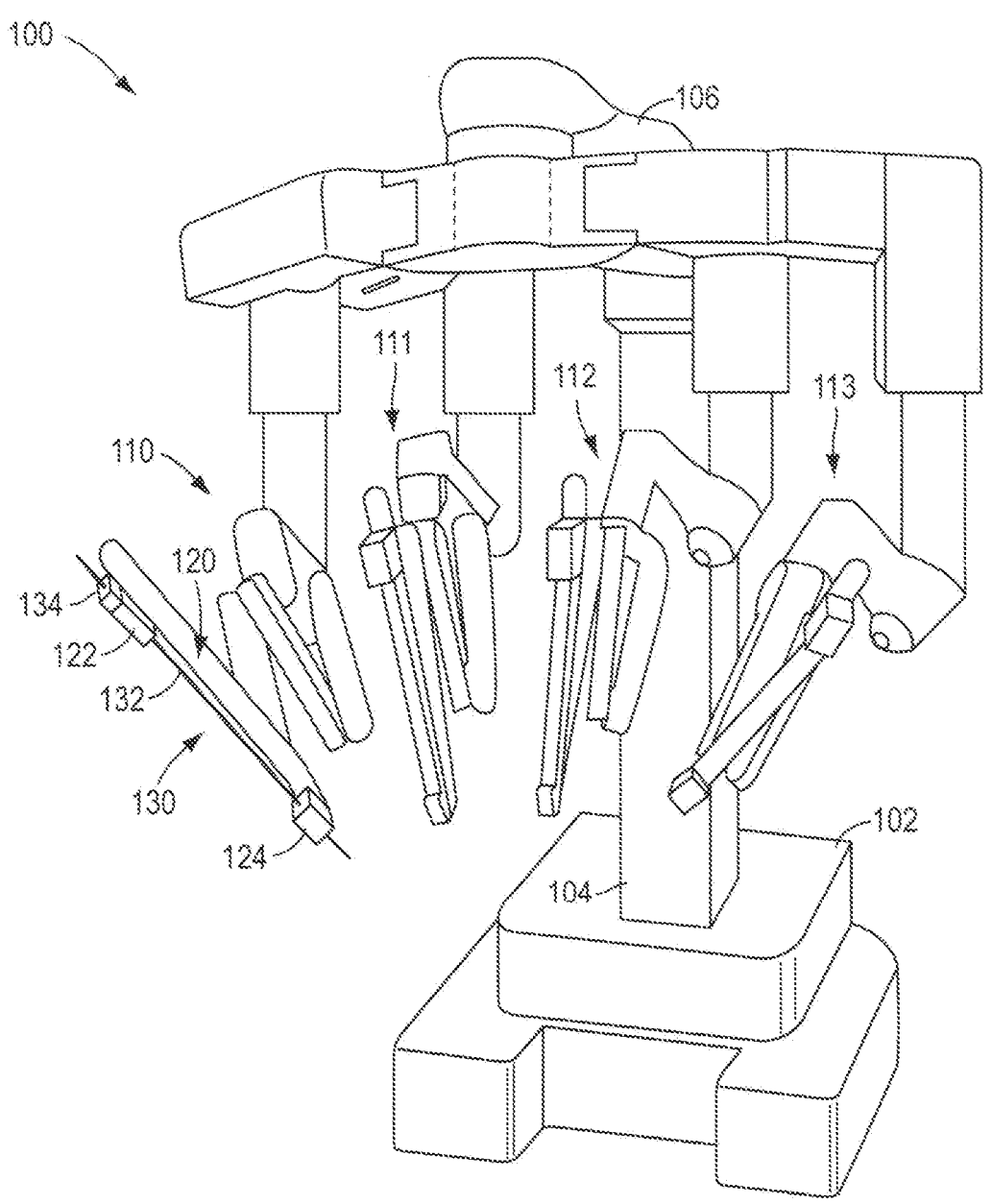
FIG. 1A is a front view of an exemplary embodiment of a patient side cart of a teleoperated surgical system.

As discussed above, in accordance with various exemplary embodiments, surgical instruments of the present disclosure are configured for use in teleoperated, computer-assisted surgical systems (sometimes referred to as robotic surgical systems). Referring now to FIG. 1A, an exemplary embodiment of a patient side cart 100 of a teleoperated, computer-assisted surgical system, to which surgical instruments are configured to be mounted for use, is shown. Such a surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "MultiPort Surgical Robotic System Architecture" and published on Dec. 5, 2013, and U.S. Pub. No. US 2013/0325031, entitled "Redundant Axis and Degree of Freedom for Hardware Constrained Remote Center Robotic Manipulator" and published on Dec. 5, 2013, each of which is hereby incorporated by reference in its entirety. Non-limiting, exemplary embodiments of teleoperated surgical systems with which the principles of the present disclosure may be utilized include the da Vinci® Si (model no. IS3000) da Vinci® Si Surgical System, Single Site da Vinci® Surgical System, or a da Vinci® Xi Surgical System, available from Intuitive Surgical, Inc. of Sunnyvale, California. However, persons having ordinary skill in the art will appreciate that the present disclosure can be applied to a variety of surgical systems including automated or manual (hand-held) laparoscopic surgical systems, or with other surgical applications.

As shown in the exemplary embodiment of FIG. 1A, patient side cart 100 includes a base 102, a main column 104, and a main boom 106 connected to main column 104. Patient side cart 100 also includes a plurality of arms 110, 111, 112, 113, which are each connected to main boom 106. Arms 110, 111, 112, 113 each include an instrument mount portion 120 to which an instrument 130 may be mounted, which is illustrated as being attached to arm 110. Portions of arms 110, 111, 112, 113 may be manipulated during a surgical procedure according to commands provided by a user at the surgeon console. In an exemplary embodiment, signal(s) or input(s) transmitted from a surgeon console are transmitted to the control/vision cart, which may interpret the input(s) and generate command(s) or output(s) to be transmitted to the patient side cart 100 to cause manipulation of an instrument 130 (only one such instrument being mounted in FIG. 1A) and/or portions of arm 110 to which the instrument 10 is coupled at the patient side cart 100.

Instrument mount portion 120 comprises an actuation interface assembly 122 and a cannula mount 124, with a force transmission mechanism 134 of the instrument 130 connecting with the actuation interface assembly 122, according to an exemplary embodiment. Cannula mount 124 is configured to hold a cannula 136 through which a shaft 132 of instrument 130 may extend to a surgery site during a surgical procedure. Actuation interface assembly 122 contains a variety of drive and other mechanisms that are controlled to respond to input commands at the surgeon console and transmit forces to the force transmission mechanism 134 to actuate the instrument 130, as those skilled in the art are familiar with.

Although the exemplary embodiment of FIG. 1A shows an instrument 130 attached to only arm 110 for ease of viewing, an instrument may be attached to any and each of arms 110, 111, 112, 113. An instrument 130 may be a surgical instrument with an end effector as discussed herein. A surgical instrument with an end effector may be attached to and used with any of arms 110, 111, 112, 113. However, the embodiments described herein are not limited to the exemplary embodiment of FIG. 1A and various other teleoperated, computer-assisted surgical system configurations may be used with the exemplary embodiments described herein.

Figure 1B:
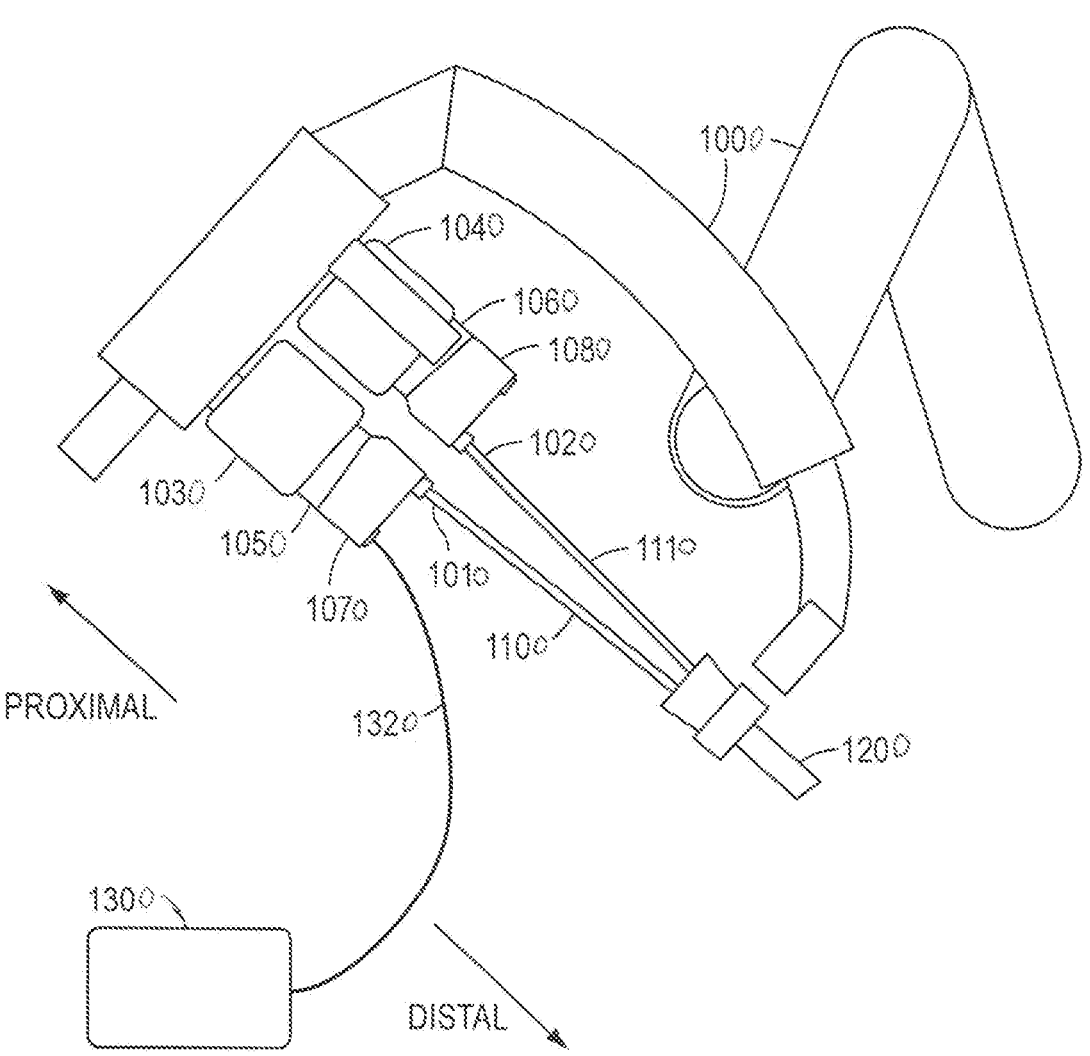
FIG. 1B is a partial schematic view of an exemplary embodiment of a manipulator arm of a patient side cart with two electrosurgical instruments in an installed position, one of which is shown in electrical communication with a flux generator.

Other configurations of surgical systems, such as surgical systems configured for single-port surgery, are also contemplated. For example, with reference now to FIG. 1B, a portion of an exemplary embodiment of a manipulator arm 1000 of a patient side cart with two surgical instruments 1010, 1020 in an installed position is shown. A teleoperated robotic surgical system, including a patient side cart comprising manipulator arm 1000, may be configured according to the exemplary embodiments described in U.S. patent application Ser. No. 14/070,184, filed Nov. 1, 2013 (for "FLUX DISAMBIGUATION FOR TELEOPERATED SURGICAL SYSTEMS"), which is incorporated by reference herein. The schematic illustration of FIG. 1B depicts only two surgical instruments for simplicity, but more than two surgical instruments may be received in an installed position at a patient side cart as those having ordinary skill in the art are familiar with. Each surgical instrument 1010, 1020 includes an instrument shaft 1100, 1110 that at a distal end has a moveable end effector (discussed below in regard to FIG. 3) or a camera or other sensing device, and may or may not include a wrist mechanism (not shown) to control the movement of the distal end.

In the exemplary embodiment of FIG. 1B, the distal end portions of the surgical instruments 1010, 1020 are received through a single port structure 1200 to be introduced into the patient. Other configurations of patient side carts that can be used in conjunction with the present disclosure can use several individual manipulator arms. In addition, individual manipulator arms may include a single instrument or a plurality of instruments. Further, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Force transmission mechanisms 1070, 1080 are disposed at a proximal end of each shaft 1100, 1110 and connect through a sterile adaptor 1050, 1060 with actuation interface assemblies 1030, 1040. Actuation interface assemblies 1030, 1040 contain a variety of internal mechanisms (not shown) that are controlled by a controller (e.g., at a control cart of a surgical system) to respond to input commands at a surgeon side console of a surgical system to transmit forces to the force transmission mechanisms 1070, 1080 to actuate instruments 1010, 1020. The diameter or diameters of an instrument shaft, wrist mechanism, and end effector are generally selected according to the size of the cannula with which the instrument will be used and depending on the surgical procedures being performed. In various exemplary embodiments, a shaft and/or wrist mechanism has a diameter of about 4 mm, 5 mm, or 8 mm in diameter, for example, to match the sizes of some existing cannula systems. According to an exemplary embodiment, one or more of surgical instruments 1010, 1020 may be in communication with a flux source 1300 via a flux transmission conduit 1320. For example, if a surgical instrument 1010 is an electrosurgical instrument, flux transmission conduit 1320 is an electrical energy transmission cable and flux source 1300 is an electrical energy generator.

Figure 2:
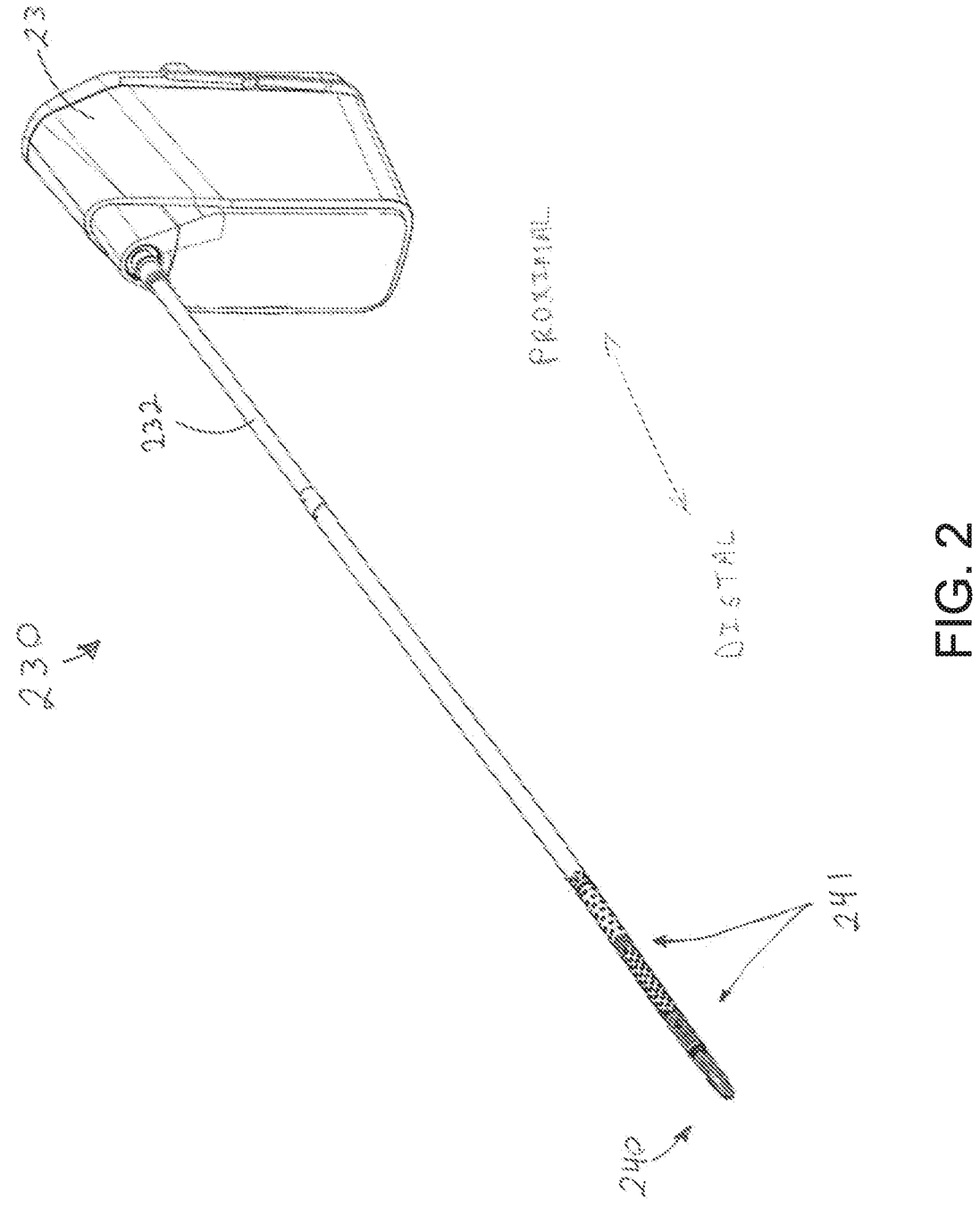
FIG. 2 is a perspective view of an exemplary embodiment of a surgical instrument.

Referring now to FIG. 2, a surgical instrument 230 according to an embodiment of the disclosure is shown. The surgical instrument 230 includes a shaft 232 with an end effector 240 positioned at a distal end thereof. The surgical instrument also includes a force transmission mechanism 234 coupled with a proximal end of the shaft 232 and configured to be operably coupled with an actuation interface assembly (e.g., actuation interface assembly 122 in FIG. 1A) of a patient side cart (e.g., patient side cart 100 in FIG. 1A). The shaft 232 may include one or more joint structures, such as wrists 241, configured to impart one or more degrees of freedom to the end effector 240.

Figure 3:
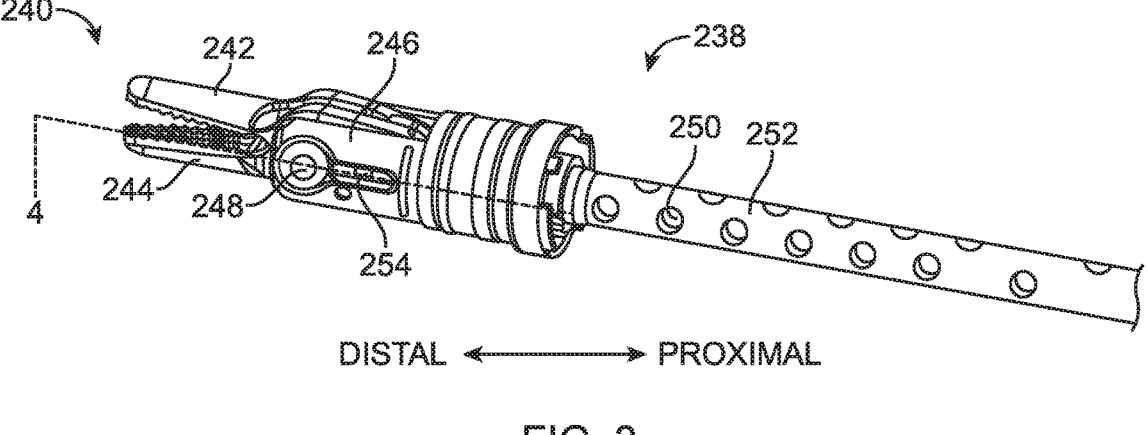
FIG. 3 is a perspective view of an interior portion of a surgical instrument including an end effector according to an exemplary embodiment.

Referring now to FIG. 3, various components of a distal end portion 238 of a surgical instrument (e.g., instrument 130 shown in FIG. 1) are shown, including an end effector 240. In an exemplary embodiment, the end effector 240 includes jaws 242 and 244 configured to perform, e.g., a gripping function. However, those having ordinary skill in the art would appreciate that other end effector configurations are contemplated, such as those used as forceps, a grasper, a needle driver, a scalpel, scissors, a stapler, a clamp, a cauterizing tool, a hook, a blade, etc. In the exemplary embodiment of FIG. 3, a pin 248 pivotably couples the jaws 242 and 244 of the end effector 240 with a clevis 246. In an exemplary embodiment, the clevis 246 may be a clevis having the configuration as shown and described in PCT Application No. PCT/US17/33529, filed May 19, 2017, which claims priority to U.S. Provisional Patent Application No. 62/362,336, entitled "SURGICAL INSTRUMENTS WITH ELECTRICALLY ISOLATED COMPONENTS, RELATED SYSTEMS AND METHODS," the entire disclosure of which is incorporated by reference herein.

A distal portion of an actuation member 250 is shown within a sleeve 252 extending proximally from the end effector 240. The actuation member 250 and sleeve 252 are positioned within a central bore of a shaft (e.g., shaft 232 in FIG. 2) of the surgical instrument; for clarity, the shaft 232 is omitted from FIG. 3 to reveal the actuation member 250 of sleeve 252. The shaft may include one or more joint structures, such as wrists 241 (FIG. 2) that impart one or more degrees of freedom to the end effector 240. The actuation member 250 is configured to translate distally and proximally relative to the clevis 246 and the shaft to actuate the end effector 240. For example, in the exemplary embodiment of FIG. 3, the actuation member 250 includes a T-head 254 configured to interact with slots (not shown) of the jaws 242, 244 to actuate (e.g., open, close) the end effector 240. The actuation member 250 connects to the force transmission mechanism 234 (FIG. 2) to transmit forces (e.g., actuation forces) between the force transmission mechanism 234 and the end effector 240.

Figure 4:
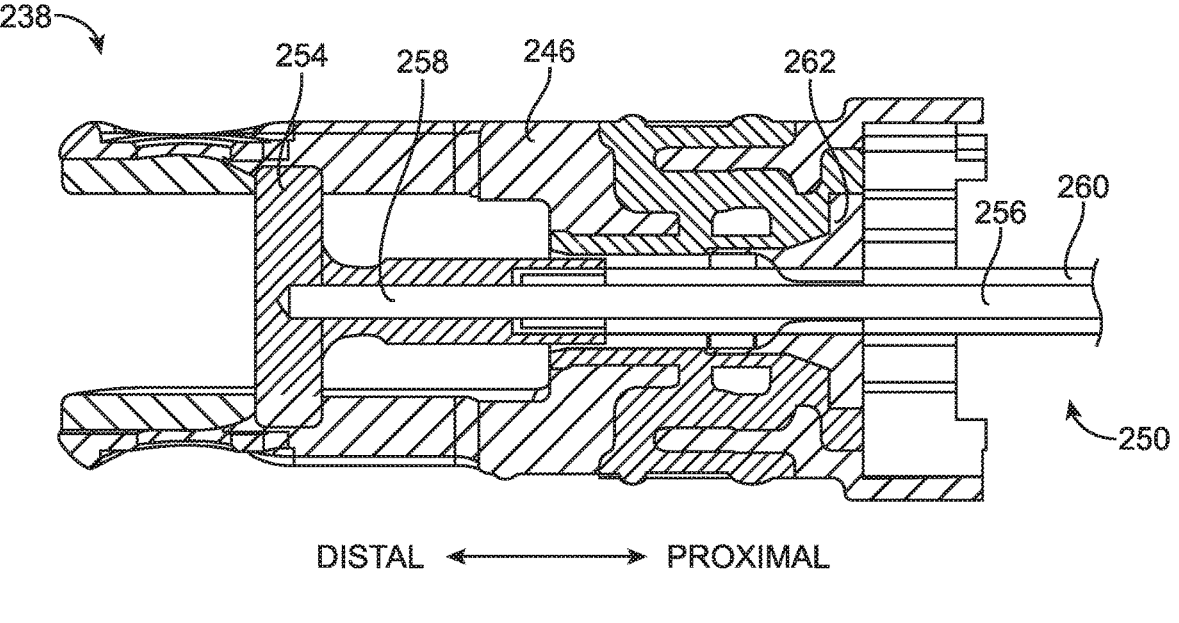
FIG. 4 is a cross-sectional view through section 4-4 of the surgical instrument of FIG. 3.

Referring now to FIG. 4, a cross-sectional view of the distal end portion 238 of the surgical instrument of FIG. 3 is shown with the jaws 242, 244 omitted for clarity. The distal portion of the actuation member 250 comprises the T-head 254 and a flexible portion 256 (which may be a flexible segment). The flexible portion 256 may comprise a cable (e.g., such as twisted or braided strands of metal or metal alloy), having a degree of flexibility sufficient to enable the flexible portion 256 to flex (e.g., bend) with the shaft 232 (FIG. 2) of the instrument 230 (FIG. 2) as one or more jointed structures (e.g., wrists 241 (FIG. 2)) of the instrument shaft 232 articulate. The flexible portion 256 can be coupled with the T-head 254 by inserting the flexible portion 256 within a bore 258 of the T-head 254 and swaging the T-head 254 over the flexible portion 256 to retain the flexible portion 256 within the bore 258 of the T-head. Other methods without limitation can be used to affix the head 254 to the flexible portion 256. Actuation (e.g., translation proximally or distally) of the actuation member 250 causes the T-head 254 to interact with slots in distal portions of the jaws 242, 244 of the end effector 240 to, e.g., open and close the end effector jaws 242, 244.

The flexible portion 256 is surrounded by (e.g., coated) with an electrically insulating material 260. For example, the electrically insulating material 260 may comprise a polymer material, a composite material, etc. In the exemplary embodiment of FIG. 4, the electrically insulating material comprises a polymer coating over the flexible portion 256 such as, for example, nylon, polytetrafluoroethylene, or another polymer or other material. In one exemplary embodiment, the electrically insulating material 260 is ethylene tetrafluoroethylene (ETFE) having a wall thickness in the range of several thousandths of an inch. For example, the electrically insulating material 260 may have a wall thickness of between 0.001 in. (0.0254 mm) and 0.1 in. (2.54 mm), such as, for example, 0.010 in. (0.254 mm). A dielectric strength of the electrically insulating material 260 may range from hundreds of volts per thousandth of an inch (V/mil) to thousands of volts per thousandth of an inch (V/mil). As a non-limiting example, the electrically insulating material 260 may have a dielectric strength ranging from about 400 V/mil to about 1800 V/mil.

The clevis 246 includes a seal 262 disposed at a proximal location of the clevis 246. The seal 262 comprises a material configured to form a liquid seal around the electrically insulating material 260 to prevent liquids or other matter present at the distal end portion 238 of the instrument 130 (FIG. 1), e.g., at a surgical site where the end effector 240 is in use. The seal 262 may comprise a material such as silicone rubber, or another electrically insulating material capable of forming a liquid seal around the electrically insulating material 260. The seal 262 may have a configuration substantially as shown and described in PCT Application No. PCT/US17/33529, filed May 19, 2017, which claims priority to U.S. Provisional Patent Application No. 62/362,336, incorporated by reference above.

As discussed above, to provide sufficient rigidity to be able to transmit force from a proximal drive of the surgical instrument down the shaft to actuate the end effector, the actuation member 250 may include a proximal portion that is relatively rigid compared to the flexible portion 256. For example, the flexible portion 256 can be used to extend through wrists or other jointed structures of the instrument shaft 232 (FIG. 2) where more bending/articulation is experienced, while a rigid portion may extend through a non-jointed portion of the instrument shaft 232.

Figure 5:
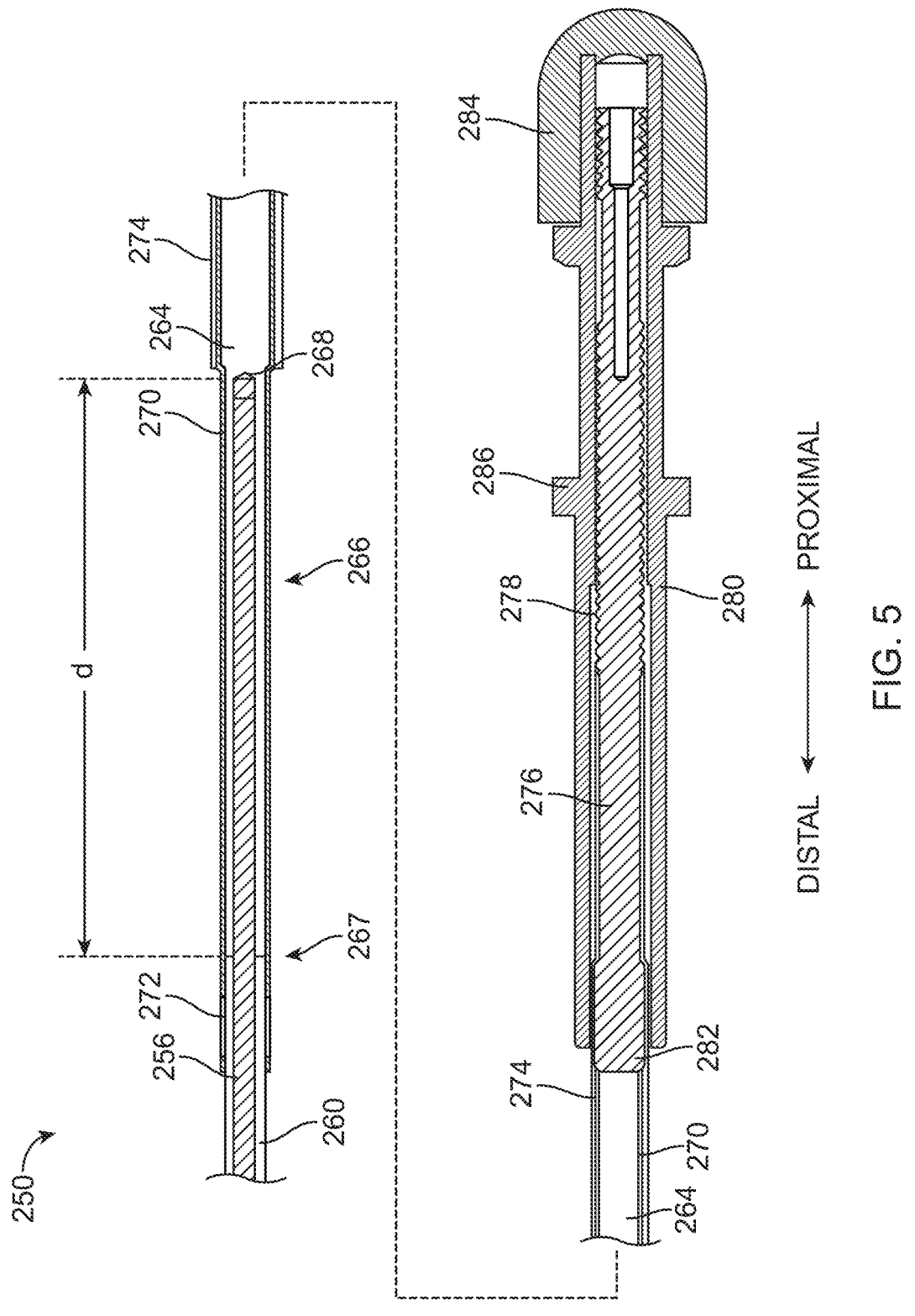
FIG. 5 is an isometric, broken cross-sectional view of an actuation member according to an exemplary embodiment of the disclosure.

For example, FIG. 5 is a cross-sectional, broken view of an actuation member 250 including the flexible portion 256 and a rigid, solid rod portion 264 coupled with the flexible portion 256. (The solid rod portion 264 may be a rod segment.) The distal end of the actuation member 250 including the head 254 (FIG. 4) is not shown in FIG. 5. To attach the flexible and rigid portions, distal end portion 266 (also "distal end 266") of the rod portion 264 includes a blind bore 268 into which the flexible portion 256 is inserted. The distal end portion 266 of the rod portion 264 is swaged over the flexible portion 256 to retain the flexible portion 256 within the bore 268 of the rod portion 264. The bore 268 extends a depth d into the rod portion 264 from a distal end 267 of the rod portion. The depth d may be chosen to ensure that the flexible portion 256 is retained in the bore 268 with a strength sufficient to withstand tensile and/or compressive loads exerted on the actuation member 250 used to actuate the end effector (e.g., end effector 240 (FIG. 2)). As a non-limiting example range of values, the depth d may range from about 0.1 in. (2.54 mm) to about 1.0 in. (25.4 mm). In one exemplary embodiment, the depth d is about 0.4" (10.16 mm).

As shown in FIG. 5, the electrically insulating material 260 surrounding the flexible portion 256 has an outside diameter approximately equal to an outside diameter of the distal end portion 266 of the rod portion 264. An electrically insulating sleeve 270 is disposed over the rod portion 264 and extends distally beyond the distal end portion 266 of the rod portion 264 so as to cover a portion of the electrically insulating material 260, thereby forming a continuous electrically insulating outer surface between the T-head 254 (FIG. 4) and the rod portion 264.

In the exemplary embodiment of FIG. 5, the electrically insulating sleeve 270 comprises a sleeve (e.g., tube) of material configured to tightly contract around the rod portion 264. For example, the electrically insulating material may be heat-shrink tubing made of, for example, nylon, polyolefin, or other heat-shrinkable and electrically insulating polymer materials. The electrically insulating sleeve 270 may have a wall thickness of, e.g., several thousandths of an inch. For example, the electrically insulating sleeve 270 may have a wall thickness of between about 0.001" (0.0254 mm and 0.010" (0.254 mm). The material of the electrically insulating sleeve 270 may exhibit a dielectric strength range of from about 500 V/mil to about 2000 V/mil. As a specific, non-limiting example, the electrically insulating sleeve 270 may be made from fluorinated ethylene propylene (FEP) and have a wall thickness of approximately 0.006 in. (0.152 mm).

A reinforcing band 272 also may be placed around the electrically insulating sleeve 270 near a distal end thereof. The reinforcing band 272 reinforces the seal of the electrically insulating sleeve 270 and helps to prevent liquid from penetrating between the electrically insulating sleeve 270 and the electrically insulating material 260. The reinforcing band 272 may be made from material similar to that of the electrically insulating sleeve 270. For example, in the exemplary embodiment of FIG. 5, the reinforcing band 272 comprises a polymer similar to that of the electrically insulating sleeve 270, e.g., FEP. In other exemplary embodiments, the reinforcing band 272 may be a spring clip, crimp sleeve, or any other structure configured to exert a compressive force around the sleeve 270 to form a seal between the electrically insulating sleeve 270 and the electrically insulating material 260.

In the exemplary embodiment of FIG. 5, the actuation member 250 further includes a secondary layer of electrically insulating material surrounding at least part the length of the rod portion 264. For example, at least part of the length of the rod portion 264 may be covered by a secondary insulating sleeve 274, made from the same or different material as the electrically insulating sleeve 270. The secondary insulating sleeve 274 may be made of, for example, a polymer such as nylon, polyolefin, or other materials. Further, in an exemplary embodiment, as with sleeve 270, the secondary insulating sleeve 274 can be a tube configured to be positioned around the rod portion 264 and contracted around the rod portion 264 and electrically insulating sleeve 270, for example, by application of heat to the tube (i.e., heat shrink tubing).

A proximal end portion 276 (also "proximal end 276") of the rod portion 264 includes features configured to maintain electrical insulation of the actuation member 250 and enable mechanical coupling of the actuation member 250 to an actuator device, e.g., an actuator associated with the force transmission mechanism 234 (FIG. 2) of the surgical instrument 230 (FIG. 2). For example, the proximal end portion 276 of the rod portion 264 may include a textured surface 278 formed on an exterior of the proximal end portion 276 of the rod portion 264 and extending along a portion of the length of the proximal end portion 276 of the rod portion 264. For example, the textured surface 278 may be provided by ribs, threads, knurling, or other suitable raised surface textures on the exterior surface of the proximal end portion 276. An electrically insulating cylinder 280 is positioned over the proximal end portion 276 of the rod portion 264 and at least partially engages with the textured surface 278, as described in greater detail below in connection with FIGS. 6A and 6B. The electrically insulating cylinder 280 at least partially overlaps one or both of the electrically insulating sleeve 270 and the secondary insulating sleeve 274 to maintain electrical insulation over the exterior of the rod portion 264. In the exemplary embodiment of FIG. 5, the electrically insulating cylinder 280 overlaps the secondary insulating sleeve 274 over an enlarged diameter section 282 of the proximal end portion 276 of the rod portion 264. Providing the rod portion 264 with the enlarged diameter section 282 adjacent to where the secondary insulating sleeve 274 terminates can assist in ensuring a tight, hermetic seal between the secondary insulating sleeve 274 and the electrically insulating cylinder 280.

The electrically insulating cylinder 280 may be made from a material having appropriate properties such as creep resistance, temperature resistance, yield strength, dielectric strength, and other properties. In an exemplary embodiment, the electrically insulating cylinder 280 is made from a material such as polyether ether ketone (PEEK). In some embodiments, the material of the electrically insulating cylinder 280 is reinforced with fibers, such as glass fibers. While a certain amount of material creep and/or yield is desirable to ensure the electrically insulating cylinder 280 deforms to at least partially match the textured surface 278 of the rod portion 264, excessive creep and/or material yield may result in insufficient dielectric strength of the electrically insulating cylinder 280. As a non-limiting example, the material of the electrically insulating cylinder 280 may exhibit a yield strength of about 100 megapascals (MPa) or more, and a dielectric strength of about 500 V/mil or more.

An endcap 284 comprising an electrically insulating material can be fit in and/or around the electrically insulating cylinder 280 to complete the electrical insulation around the rod portion 264. The endcap 284 may comprise any electrically insulating material, such as the polymer materials noted above, other polymers such as silicone rubber, etc.

In the exemplary embodiment of FIG. 5, the electrically insulating cylinder 280 includes one or more annular collars 286 extending radially outward from a proximal portion of the electrically insulating cylinder 280. The annular collars 286 may serve to locate and/or engage a clamp configured to couple the actuation member 250 with an actuator of a force transmission mechanism such as force transmission mechanism 234 (FIG. 2).

Figure 6A:
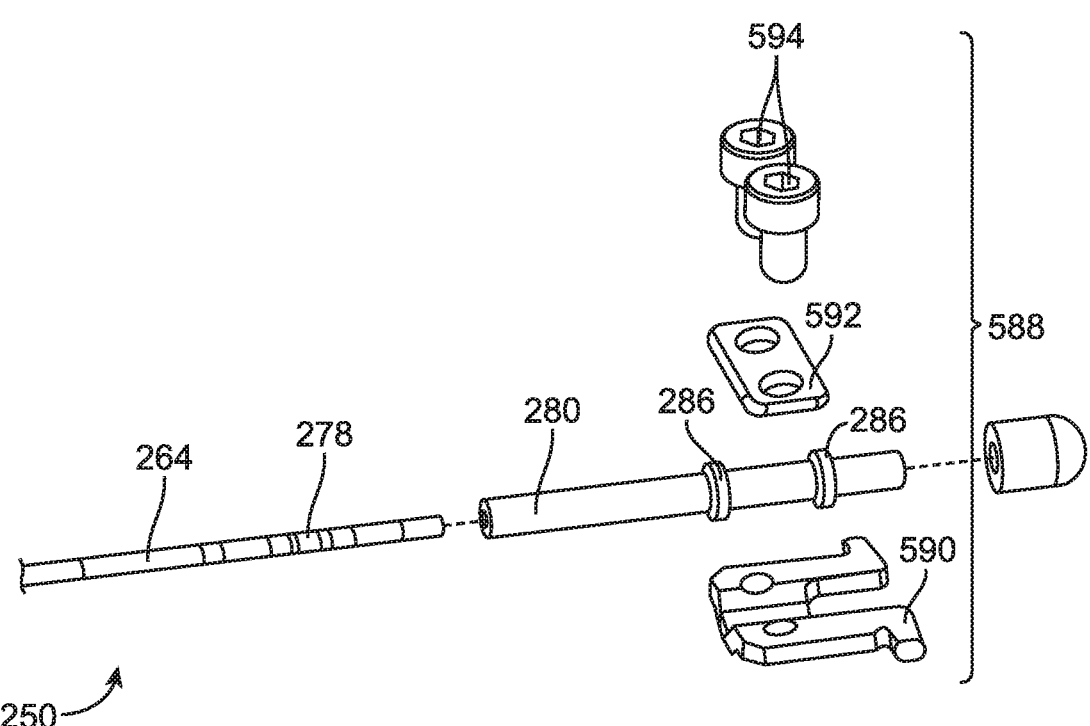
FIG. 6A is an exploded view of a proximal portion of an actuation member and a clamp member according to an exemplary embodiment of the disclosure.
Figure 6B:
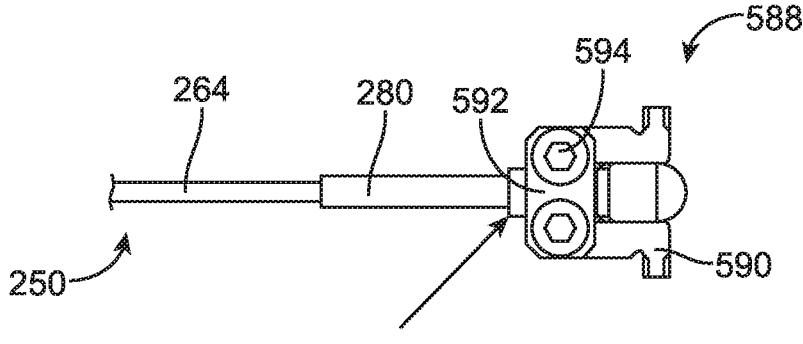
FIG. 6B is a partial, plan view of the actuation member and clamp member of the embodiment of FIG. 6A.

For example, referring now to FIG. 6A, an actuation member 250 and clamp assembly 588 according to an exemplary embodiment are shown in an exploded view. The clamp assembly 588 includes a link bracket 590 configured to couple with an actuator of the force transmission mechanism 134 (FIG. 1), as described below in connection with FIGS. 8A and 8B. A clamp plate 592 is fastened to the link bracket 590 with fasteners, such as, for example, cap screws 594 threaded into the link bracket 590. Tightening the cap screws 594 draw the clamp plate 592 and link bracket 590 together over the electrically insulating cylinder 280 as shown in FIG. 6B, clamping and compressing the electrically insulating cylinder 280 over the proximal end portion 276 of the rod portion 264 and causing the textured surface 278 to at least partially deform to match the profile of the textured surface 278. Stated differently, the textured surface 278 "bites" into an interior surface of the electrically insulating cylinder 280 as the clamp plate 592 and link bracket 590 are tightened over the electrically insulating cylinder 280, as shown in FIG. 6B. The annular collars 286 of the electrically insulating cylinder 280 prevent axial movement of the clamp assembly 588 relative to the electrically insulating cylinder 280.

Figure 7:
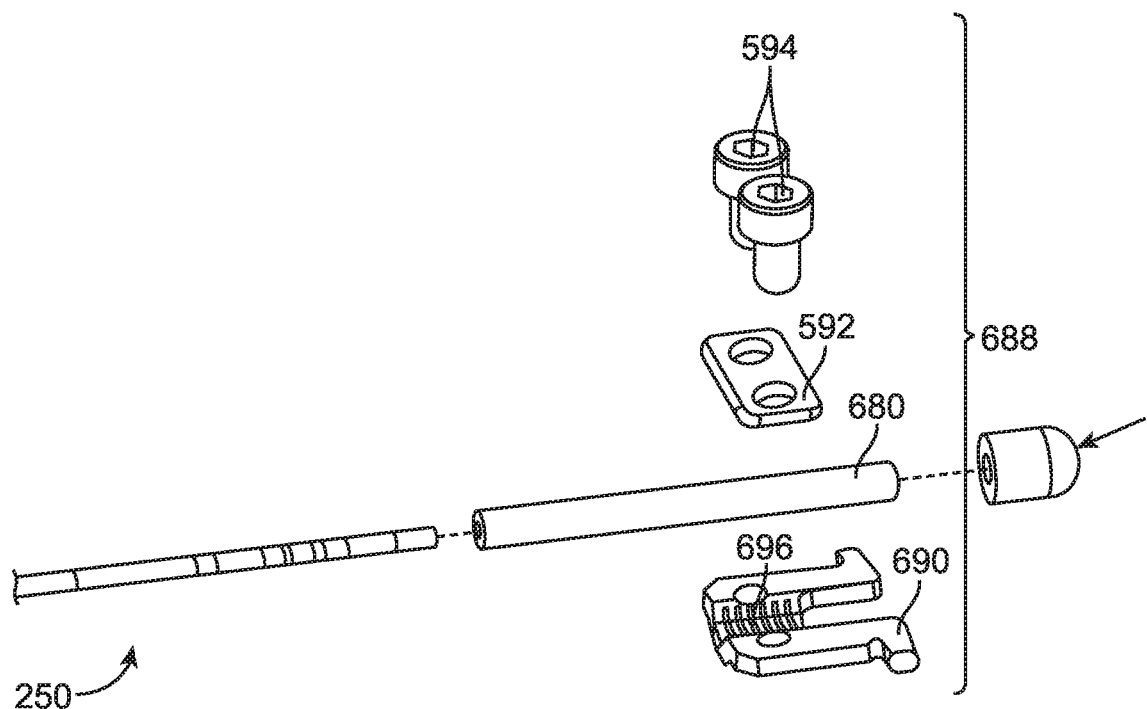
FIG. 7 is an exploded view of a proximal portion of an actuation member and a clamp member according to another exemplary embodiment of the disclosure.

FIG. 7 shows an actuation member 250 and clamp assembly 688 according to another exemplary embodiment of the disclosure. In the exemplary embodiment of FIG. 7, the electrically insulating cylinder 680 does not include annular collars 286 of the embodiments of FIGS. 5 through 6B, and rather has a substantially uniform outer dimension (e.g., outer diameter). A link bracket 690 includes internal ridges 696 positioned to contact the electrically insulating cylinder 680. The ridges 696 grip the electrically insulating cylinder 680 and prevent the clamp assembly 688 from slipping axially on the electrically insulating cylinder 680 when the clamp plate 592 and link bracket 690 are tightened over the electrically insulating cylinder 680.

The link brackets 590, 690 and clamp plate 592 may comprise metal or metal alloy materials. In the embodiments shown in FIGS. 5 through 7, the link brackets 590, 690 and the clamp plate 592 have rounded edges to prevent any portion of the link bracket 590, 690, or the clamp plate 592, from cutting through the electrically insulating cylinders 580, 680 and forming a conductive path with (e.g., contacting) the rod portion 264 when the cap screws 594 are tightened.

Figure 8A:
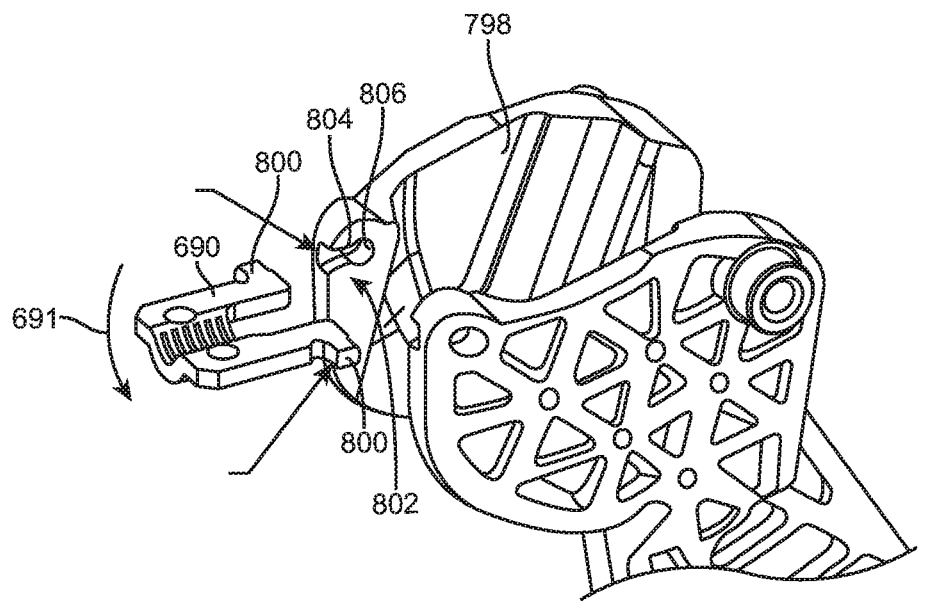
FIG. 8A is a perspective view of a portion of a clamp member and an actuator in an unassembled state according to an exemplary embodiment of the disclosure.

Referring now to FIG. 8A, a link bracket 690 and an actuator lever 798, which may form a portion of (e.g., be a component of) a force transmission mechanism 134 (FIG. 1), is shown. Stub axles 800 of the link bracket 690 have a flattened cylindrical cross section. Slots 802 in the actuator lever 798 include a narrowed neck portion 804 and a rounded bore 806. With the relative orientation between the link bracket 690 and the actuator lever 798 shown in FIG. 8A, the flattened portion enables the stub axles 800 to slide into slots 802 past the narrowed neck portion 804. Once the stub axles 800 of the link bracket 690 enter the slots 802, the link bracket 690 is pivoted downward as indicated by arrow 691, and the stub axles 800 are retained within the rounded bores 806 of the slots 802 by the narrowed neck portion 804.

Figure 8B:
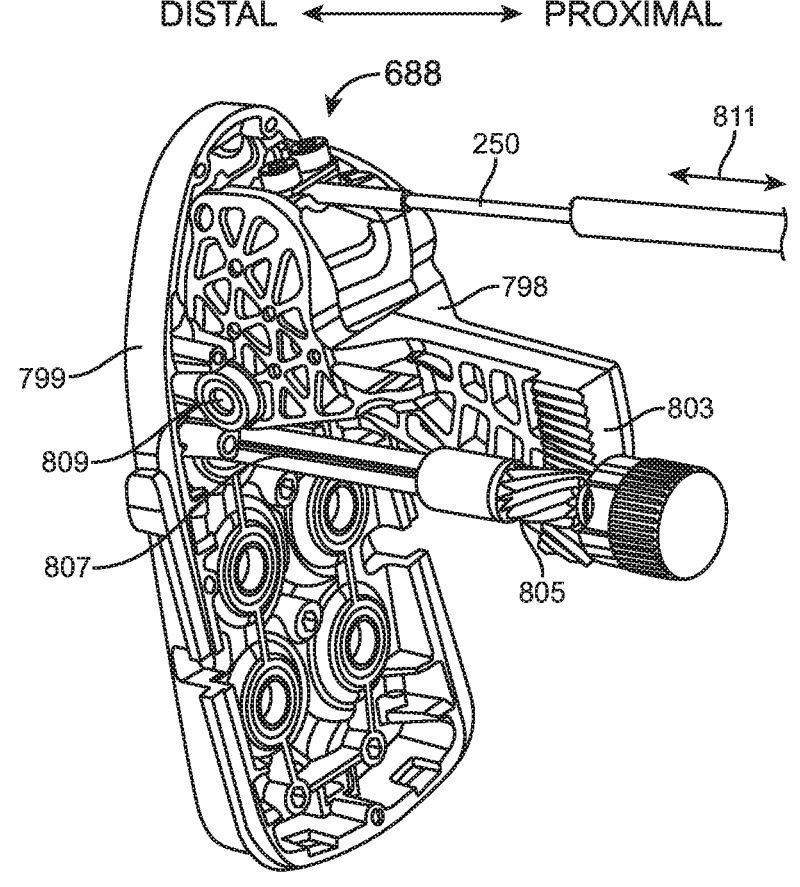
FIG. 8B is a perspective view of the portion of the clamp member and the actuator of FIG. 8A in an assembled state.

Referring now to FIG. 8B, the clamp assembly 688 (FIG. 7), the actuation member 250, and the actuator lever 798 are shown assembled with a portion of a chassis 799 of a force transmission mechanism (e.g., force transmission mechanism 234 shown in FIG. 2), with the outer cover of the housing of the force transmission mechanism removed to see the internal components thereof. The actuator lever 798 comprises a sector gear 803 meshed with a pinion gear 805. The pinion gear 805 is affixed to a driveshaft 807, which may be operably coupled with a drive mechanism of the patient side cart 100, such as an actuation interface assembly 122 (FIG. 1). For example, in an exemplary embodiment, the driveshaft 807 is configured to be driven by a motor of the actuation interface assembly 122 when the chassis 799 is in an installed position on the patient side cart 100. The actuator lever 798 is pivotally affixed to the chassis 799 by bearings 809. Rotation of the pinion gear 805 causes pivoting movement of the actuator lever 798 about the bearings 809, which movement generates translational movement (in directions 811) of the actuation member 250 coupled with the actuator lever 798 by the clamp assembly 688. The force transmission mechanism 234 and related components may be configured according to, for example, any of the exemplary embodiments shown and described in at least in U.S. Patent App. Pub. No. US2014/0338477, published Nov. 20, 2016, and entitled "FORCE TRANSMISSION MECHANISM FOR TELEOPERATED SURGICAL SYSTEM," and PCT Application No. PCT/US17/38343, filed Jun. 20, 2017, which claims priority to U.S. Provisional Patent Application No. 62/362,365, entitled "GEARED GRIP ACTUATION FOR MEDICAL INSTRUMENTS," the entire contents of each of which are incorporated by reference herein.

The electrical insulation of the actuation member 250 (e.g., via electrically insulating cylinder 680) permits the clamp assembly 588, 688 to be made of metal material to provide a robust connection between the actuation member 250 and the actuation lever 798 of the transmission mechanism. In view of the relatively tight clearances where the grip rod is connected to the actuation lever 798 within the transmission housing, if the grip rod were not electrically insulated from the clamp assembly 588, 688, then the metal clamp would potentially provide an electrically conductive pathway from the distal end of the surgical instrument to various cables, pulleys, and other components in the transmission mechanism/chassis 799. The ability to make the clamp assembly 588, 688 out of metal permits the clamp to be made by relatively inexpensive processes, such as stamping, for example, and to be made relatively small in dimensions while providing adequate stiffness/strength, thereby allowing the clamp to fit in a relatively small space within the force transmission mechanism where many components are located and it is desirable to optimize space. Metal also permits the clamp to be provided with screw threads with screws installed to high torque, resulting in high clamping forces on the actuation member. Moreover, the axle of the pivoting part of the clamp assembly may be hard and small diameter so that it provides a smooth low friction bearing surface of the actuation lever 798, including the sector gear 803 without additional bearings.

Figures 9, 10:
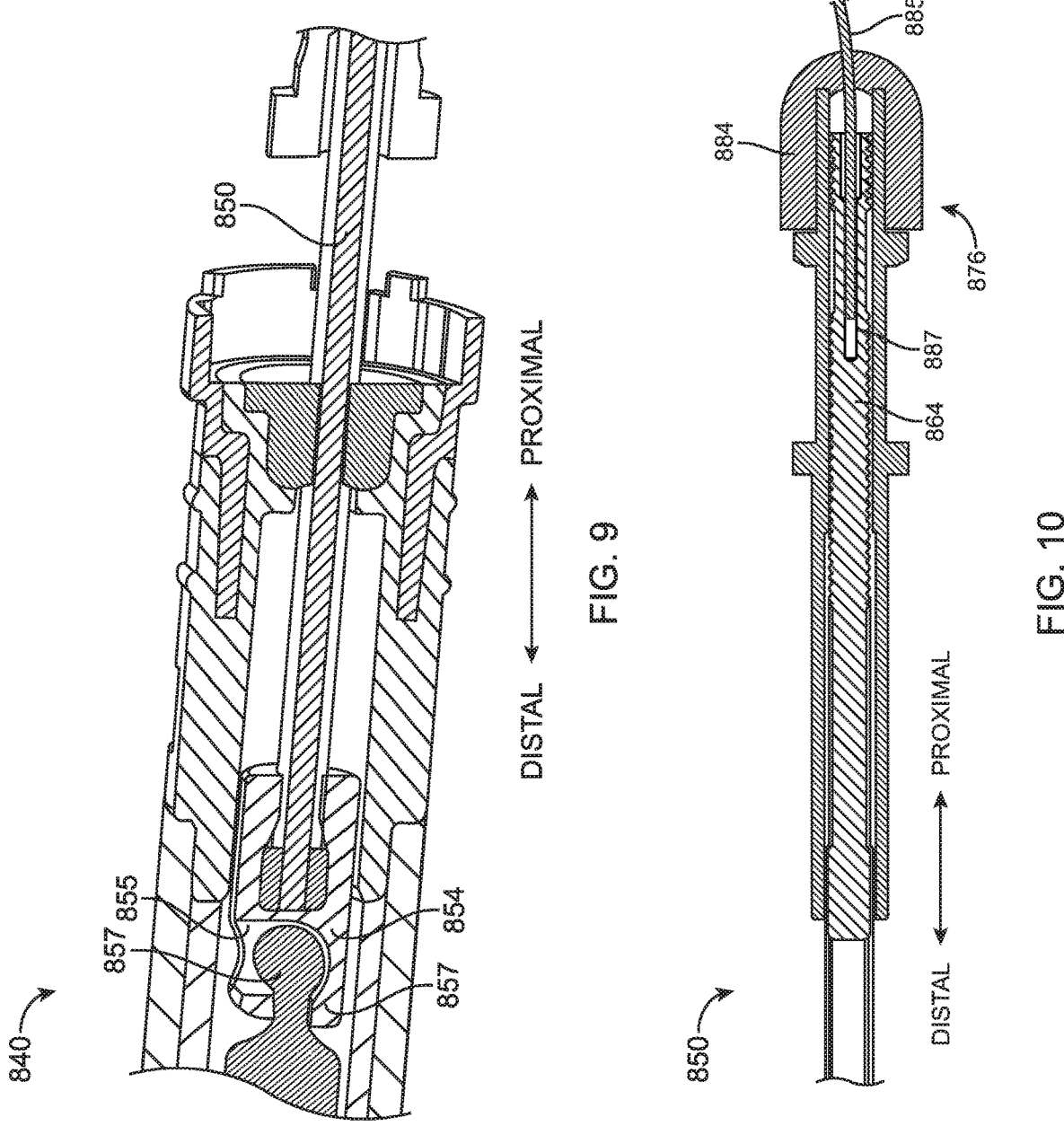
FIG. 9 is a cross-sectional view of a portion of an end effector component of a surgical instrument according to yet another exemplary embodiment of the disclosure.
FIG. 10 is a cross-sectional view of an actuation member according to yet another exemplary embodiment of the disclosure.

FIG. 9 shows a cross-sectional view of an end effector portion 840 (also "end effector 840") according to an exemplary embodiment alternative to the embodiments of FIGS. 3 and 4. In the embodiment of FIG. 9, an actuation member 850 includes a head 854 with a socket portion 855 configured to accept a complementary component, such as a ball portion 857. For example, the end effector portion 840 may be a portion of an end effector of a surgical instrument such as those shown and described in Intl Pub. No. WO 2015/023865, filed Aug. 14, 2014, and titled "REUSABLE SURGICAL INSTRUMENT WITH SINGLE-USE TIP AND INTEGRATED TIP COVER," the disclosure of which is incorporated by reference herein in its entirety.

In exemplary embodiments, such surgical instruments may be configured to apply electrical current at a surgical site by bringing a component of the end effector to a voltage potential different from a reference potential (e.g., zero potential, ground, etc.) of a patient's body. In such embodiments, an electrically insulated actuation member 850 (e.g., actuation member 250 shown in FIGS. 2 through 6), may be used to conduct an electrical current between the end effector (e.g., an end effector associated with the end effector portion 840 shown in FIG. 9) and another portion of the surgical instrument, such as a surgical instrument patient side cart 100 (FIG. 1) or other source of electrical energy. For example, in the exemplary embodiment of FIG. 10, an electrical conductor 885 extends through an electrically insulating endcap 884 positioned over a proximal end 876 of the actuation member 850. The electrical conductor 885 is inserted within a blind bore 887 of a rod portion 864 of the actuation member 850, and the rod portion 864 is crimped over the electrical conductor 885 to retain the electrical conductor in the blind bore 887 and form a conductive path between the electrical conductor 885 and the rod portion 864. Electrical energy may be conducted through the electrically conductive rod portion 864 and an electrically conductive flexible portion (e.g., flexible portion 256 shown in FIGS. 4 and 5) to an end effector, such as end effector 840 (FIG. 9).

Actuation members according to exemplary embodiments of the disclosure provide electrical insulation between exterior distal and proximal portions of the actuation member, while enabling portions of the actuation member to be constructed from metals or metal alloys with relatively high tensile strength, hardness, and/or toughness compared to electrically insulating materials. Such construction thereby provides reliable operation and longevity due to the material characteristics of the metals/alloys and electrical insulation between the proximal and distal portions. Such actuation members may also provide a conductive path between distal and proximal portions of the surgical instrument insulated from surrounding components and tissue to facilitate application of electrical energy.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. An actuation member for transmitting force from a drive mechanism to an end effector of a surgical instrument, the actuation member having a length extending from a proximal end to a distal end, the actuation member comprising:

an electrically conductive distal flexible portion extending proximally from the distal end of the actuation member and configured to be operably coupled with the end effector of the surgical instrument;

an electrically conductive proximal rod portion connected to and extending proximally from the distal flexible portion, the proximal rod portion being configured to be operably coupled to the drive mechanism, the proximal rod portion comprising a blind bore in which a proximal end portion of the distal flexible portion is received, the distal flexible portion in electrically conductive communication with the electrically conductive proximal rod portion, and the proximal rod portion having a solid cross-section proximally of a terminating end of the blind bore;

a first electrically insulating material surrounding at least some of a length of the distal flexible portion that is not received in the blind bore;

a second electrically insulating material overlapping the first electrically insulating material and surrounding at least some of a length of the proximal rod portion from a location where the proximal rod portion connects to the distal flexible portion and to a location where the proximal rod portion is solid;

an electrically insulating sleeve overlapping at least a portion of the second electrically insulating material and extending proximally past the second electrically insulating material along a length of the proximal rod portion that is solid; and an electrically insulating cylinder overlapping at least a portion of the electrically insulating sleeve and positioned over a proximal end portion of the proximal rod portion.

2. The actuation member of claim 1, wherein at least one of the first and second electrically insulating materials comprise a heat-shrinking polymer material.

3. The actuation member of claim 1, wherein the electrically insulating cylinder extends over a textured surface of the proximal rod portion.

4. The actuation member of claim 3, wherein the textured surface of the proximal rod portion is configured to engage an interior surface of the electrically insulating cylinder by partially deforming the electrically insulating cylinder.

5. The actuation member of claim 1, wherein the electrically insulating cylinder comprises one or more features configured to locate a clamp of the drive mechanism.

6. The actuation member of claim 5, wherein the features comprise one or more annular collars extending radially outward from a proximal portion of the electrically insulating cylinder.

7. The actuation member of claim 1, wherein at least one of the electrically conductive distal flexible portion and the electrically conductive proximal rod portion comprise a material chosen from a metal and a metal alloy.

8. The actuation member of claim 1, wherein the actuation member is configured to conduct an electrical flux from an electrical energy source operably connected to the proximal end of the proximal rod portion to at least one electrode associated with the end effector.

9. The actuation member of claim 8, further comprising an electrical conductor retained in the proximal rod portion and extending from the proximal end of the proximal rod portion, the electrical conductor configured to electrically connect to the electrical energy source.

10. The actuation member of claim 1, further comprising a reinforcing band positioned over the second electrically insulating material and configured to exert a compressive force around the second electrically insulating material, the reinforcing band being further configured to maintain a liquid seal between the first electrically insulating material and the second electrically insulating material.

11. The actuation member of claim 1, wherein the first electrically insulating material is a coating.

12. The actuation member of claim 1, further comprising a clevis comprising a seal disposed at a proximal location of the clevis, where the seal comprises a material configured to form a liquid seal around the first electrically insulating material.

13. The actuation member of claim 1, wherein the blind bore extends into the proximal rod portion up to a depth retaining the flexible portion in the blind bore with a strength sufficient to withstand compressive loads exerted on the actuation member to transmit force to actuate the end effector.

14. The actuation member of claim 1, further comprising an end cap comprising an electrically insulating material and overlapping with a portion of the electrically insulating cylinder.

15. The actuation member of claim 1, wherein an exterior of the proximal rod portion has a textured surface, and wherein the electrically insulating cylinder is deformable to mate with the textured surface.

16. The actuation member of claim 1, wherein the electrically insulating cylinder comprises a material exhibiting a yield strength of more than 100 megapascals (MPa) and a dielectric strength of more than 500 V/mil.

17. The actuation member of claim 1, wherein the electrically insulating cylinder comprises a material reinforced with glass fiber.

* * * * *